US008337774B2

(12) United States Patent
Pendergrass et al.

(10) Patent No.: US 8,337,774 B2
(45) Date of Patent: *Dec. 25, 2012

(54) COMPOSITIONS FOR SIMULTANEOUS DETECTION OF VOLATILE SULFUR COMPOUNDS AND POLYAMINES

(75) Inventors: James C. Pendergrass, Lexington, KY (US); Boyd E. Haley, Nicholasville, KY (US)

(73) Assignee: ALT BioScience, LLC, Lexington, KY (US)

( * ) Notice: Subject to any disclaimer, the term of this patent is extended or adjusted under 35 U.S.C. 154(b) by 1122 days.

This patent is subject to a terminal disclaimer.

(21) Appl. No.: 11/636,803

(22) Filed: Dec. 11, 2006

(65) Prior Publication Data

US 2007/0259332 A1    Nov. 8, 2007

Related U.S. Application Data

(62) Division of application No. 10/274,058, filed on Oct. 18, 2002, now Pat. No. 7,723,118.

(51) Int. Cl.
*G01N 33/00* (2006.01)

(52) U.S. Cl. .................. 422/408; 423/178; 423/174

(58) Field of Classification Search ............... 422/56, 422/58, 61, 68.1, 99, 408; 436/178, 174
See application file for complete search history.

(56) References Cited

U.S. PATENT DOCUMENTS

| 3,119,668 A | 1/1964 | Ellman |
| 3,318,910 A | 5/1967 | Williams |
| 4,334,540 A | 6/1982 | Preti et al. |
| 4,578,357 A | 3/1986 | Melpolder |
| 5,093,475 A | 3/1992 | Carroll et al. |
| 5,187,105 A | 2/1993 | Albarella et al. |
| 5,330,898 A | 7/1994 | Bar-Or et al. |
| 5,652,237 A * | 7/1997 | Augelli-Szafran et al. .................. 514/230.5 |
| 5,910,447 A | 6/1999 | Lawrence et al. |
| 6,255,066 B1 | 7/2001 | Louderback |
| 6,436,658 B1 | 8/2002 | Seman |
| 7,723,118 B2 * | 5/2010 | Pendergrass et al. ......... 436/111 |
| 2001/0056246 A1 | 12/2001 | Rodriguez-Fernandez et al. |
| 2002/0102627 A1 | 8/2002 | Lorber |
| 2002/0120406 A1 | 8/2002 | Lorber |
| 2004/0029171 A1 | 2/2004 | Wagner et al. |
| 2004/0076584 A1 | 4/2004 | Pendergrass |
| 2010/0291699 A1 | 11/2010 | Pendergrass |

FOREIGN PATENT DOCUMENTS

| JP | 57-148252 | 9/1982 |
| WO | WO 97/05482 | 2/1997 |

OTHER PUBLICATIONS

Singh, Anal. Biochem. Apr. 5, 1996; 236(1):114-125.
Gergel, Arch. Bichem. Biophys. Nov. 15, 1997; 347(2):282-288.
Lamster, Arch. Oral Biol. 1987: 32(5):329-333.
King, Biochemistry Apr. 18, 1978; 17(8):1499-1506.
Aboshama, J. Dairy Sci. Sep. 1977; 60(9):1374-1378.

* cited by examiner

*Primary Examiner* — Sam P Siefke
(74) *Attorney, Agent, or Firm* — Viksnins Harris & Padys PLLP

(57) ABSTRACT

Disclosed are compositions and methods useful for the rapid and facile simultaneous detection of malodorous bacterial metabolites in samples of expired breath and other fluids. The invention enables estimation, by simple visual inspection and comparison against standards, of the concentration of polyamines and volatile sulfur compounds in the micromolar to millimolar range.

5 Claims, No Drawings

COMPOSITIONS FOR SIMULTANEOUS DETECTION OF VOLATILE SULFUR COMPOUNDS AND POLYAMINES

CROSS REFERENCE TO RELATED APPLICATION

The present application is a division of U.S. patent application Ser. No. 10/274,058 titled Compositions And Methods For Simultaneous Detection Of Volatile Sulfur Compounds And Polyamines and filed on Oct. 18, 2002 now U.S. Pat. No. 7,723,118.

FIELD OF THE INVENTION

The invention relates to, among other fields, the field of diagnostic tests to detect the presence of pathogenic microorganisms.

BACKGROUND OF THE INVENTION

In normal circumstances many microorganisms live on or in humans without causing harm to these humans. However, an increased number of certain microorganisms can be associated with a disease state. Particularly problematic is an increase in the number of microorganisms that produce significant concentrations of chemicals that are toxic to humans. Such toxins include: volatile sulfur compounds (VSCs), such as hydrogen sulfide, methyl mercaptan, dimethyl disulfide, and dimethyl sulfide; and polyamines, such as putrescine and cadaverine. Higher concentrations of volatile sulfur compounds and of polyamines are associated with certain disease states and with socially stigmatized conditions, such as halitosis, or bad breath. It would be desirable to enable facile simultaneous detection of volatile sulfur compounds and polyamines in order to facilitate detection of the presence of potentially pathogenic microorganisms and of disease states and conditions with which these microorganisms are associated.

The principal VSCs produced by oral bacteria are hydrogen sulfide ($H_2S$) and methylmercaptan ($CH_3SH$). $H_2S$ is produced by the bacterial enzyme L-cysteine desulthydrase, which degrades the amino acid L-cysteine to produce $H_2S$, ammonium and 2-ketopropanate. The other major VSC, $CH_3SH$, is produced by the action of the bacterial enzyme L-methionine gamma lyase, which breaks down the amino acid L-methionine to produce $CH_3SH$, ammonium and 2-ketobutyrate. $H_2S$ levels have been reported to occur at levels as high as 2 mM in the gingival crevice of persons with severe periodontal disease.

In addition to VSCs, oral bacteria have also been shown to produce high levels of polyamines; chief among these are 1,4-diaminobutane(putrescine) and 1,5-diaminopentane (cadaverine). Putrescine is produced by the action of the bacterial enzyme ornithine decarboxylase, which degrades the amino acid L-ornithine to produce putrescine and carbon dioxide. Cadaverine is produced by the bacterial enzyme lysine decarboxylase, which breaks down the amino acid L-lysine to cadaverine and carbon dioxide.

Millimolar levels of these malodorous bacterial waste products have been reported in the gingival crevicular fluid (GCF) of persons with severe periodontal disease. Their presence imparts a foul odor to the breath of persons with the disease. In addition to being malodorous, VSCs have also been shown to be toxic and adversely affect a number of mammalian enzymes. Production of these waste products by bacteria residing on the dorsum of the tongue imparts a foul odor to expired breath, resulting in halitosis. Together these two classes of bacterial waste products combine to impart a foul odor to the breath of persons with halitosis and periodontal disease. The levels of these waste products in GCF correlate directly with the level of periodontal disease activity. The levels of these waste products in expired air correlate directly with the level of bad breath or halitosis.

SUMMARY OF THE INVENTION

Accordingly, the invention provides compositions and methods for simultaneous detection of volatile sulfur compounds and polyamines.

The invention provides inter alia a chromogenic (calorimetric) biochemical assay to detect volatile sulfur compounds (VSCs) and polyamines produced by oral bacteria residing on the dorsum of the tongue and in the gingival crevice.

The invention provides inter alia an assay to detect VSCs and polyamines in saliva and expired breath.

In an aspect of the invention, the absorbance of a chromogenic composition according to the invention correlates directly with the concentration of VSCs and polyamines in a fluid with which the composition is intermixed.

DETAILED DESCRIPTION OF THE INVENTION

At the outset of the description, it is helpful to note the meaning of each of several terms recurring throughout the specification and claims.

When used in connection with the invention, a "volatile sulfur compound" or. "VSC" refers to a composition having a thiol or —SH functional group or to a composition having a thiolate or sulfide anion. Examples of VSCs include hydrogen sulfide and methyl mercaptan (methanethiol).

When used in connection with the invention, "polyamine" has its usual meaning in the biochemical arts and includes a composition of the general formula $NH_2RNH_2$. Examples of polyamines include putrescine and cadaverine.

When used in connection with the invention, "DTNB" refers to 5,5'-Dithiobis(2-nitrobenzoic acid). DTNB is also known as Ellman's reagent and has CAS number 69-78-3.

When used in connection with the invention, "2-IT" refers to 2-Iminothiolane. 2-Iminothiolane hydrochloride is known as Traut's reagent and has CAS number 4781-83-3.

The invention provides inter alia a chromogenic (calorimetric) biochemical assay to detect volatile sulfur compounds (VSCs) and polyamines produced by oral bacteria residing on the dorsum of the tongue and in the gingival crevice.

The invention provides inter alia an assay to detect VSCs and polyamines in saliva and expired breath.

In an aspect of the invention, the absorbance of a chromogenic composition according to the invention correlates directly with the concentration of VSCs and polyamines in a fluid with which the composition is intermixed.

In an embodiment, the invention provides a chemically stabilized, buffered composition comprising 5,5'-Dithiobis (2-nitrobenzoic acid) (DTNB) to detect VSCs and 2-Iminothiolane (2-IT) to detect polyamines. In this regard, DTNB and other so-called sulfhydryl reagents are examples of VSC-reactive means, and 2-IT and other thiolating reagents which modify primary amino groups are examples of polyamine-reactive means.

In a particular embodiment, a composition according to the invention contains 0.5 millimolar (0.5 mM) DTNB and 0.5 mM 2-IT in 20 mM imidazole or 20 mM sodium phosphate, pH 7.0 buffer containing 0.1 mM manganese chloride ($MnCl_2$). Such composition is referred to infra as "reagent mixture." Without intending to be bound by theory, it is observed that, in such an embodiment, such concentration of $MnCl_2$ and such buffer and such pH are associated with particularly favorable stability, such that the shelf-life of the reagent mixture is 12 months or longer when stored at room temperature. A similar embodiment, in which a composition according to the invention contains 0.1 mM cobalt chloride or 0.1 mM magnesium chloride instead of the aforementioned 0.1 mM manganese chloride, also possesses particularly favorable stability. In this regard, imidazole buffer around pH 7, phosphate buffer around pH 7, manganese chloride, magnesium chloride, and cobalt chloride are examples of shelf-life-enhancing means. Theory notwithstanding, it is noted that magnesium is an alkaline earth metal and that managese and cobalt are transition metals.

Without intending to be bound by theory, it is known in the art that DTNB reacts with the sulfide or thiolate anion formed from the —SH functional group present in $H_2S$ or $CH_3SH$. In such reaction, one of the disulfide sulfurs of DTNB is attacked by the $HS^-$ or $CH_3S^-$ anion, whereupon the 5-thio-2-nitrobenzoate anion (TNB) is released. TNB exists in equilibrium with the tautomeric thioquinone. The thioquinone has an absorption (absorbance) maximum at 412 nm with a molar extinction coefficient of 13,600 $M^{-1}$ $cm^{-1}$. This allows for the reaction to be quantified spectrophotometrically or visually by the increase in the yellow color of the mixture.

While in the art the calorimetric reaction of DTNB may be regarded as optimally performed at pH 8.0, DTNB is unstable when stored for several days at room temperature under such conditions. It was unexpectedly found that the inclusion of metal salt and the adjustment of pH around neutrality impart the favorable property of a markedly extended shelf-life. By way of example and not of limitation, it was found that a DTNB mixture was maintained stable for more than one year at room temperature when the mixture included phosphate or imidazole buffer, pH 7.0, and 0.11 mM $MnCl_2$. Hence the invention provides inter alia a chromogenic composition the absorbance of which correlates directly with the concentration of VSCs in a fluid with which the composition is intermixed and which composition has a shelf-life of at least one year.

It is known in the art that 2-IT thiolates primary amines under appropriate conditions. A composition according to the invention is useful for the detection of primary amines, including polyamines, such as the malodorous diamines putrescine and cadaverine. When a composition according to the invention is intermixed or otherwise contacted with a sample that contains diamines, 2-IT of the composition reacts with primary amino (—$NH_2$) groups of the sample's diamines to yield a reaction product with at least one free sulfhydryl group. Such a free sulflhydryl group, or its thiolate anion, reacts with DTNB of the reagent mixture, releasing the TNB anion and causing an increase in absorbance at 412 nm.

Compositions and methods according to the invention are useful for detecting the presence of malodorous toxins produced by bacteria residing on the dorsum of the tongue and in GCF obtained from the gingival sulcus.

For example, in an aspect of a method according to the invention, tongue scrapings are obtained by gently rubbing the cotton tip of a sterile, cotton-tipped applicator against the dorsum of the tongue to form a scraping-laden applicator tip. The scraping-laden applicator tip is then contacted for 2 minutes at room temperature with a volume of 0.1 ml of reagent mixture contained within a sterile, screw-capped 1.5 ml microcentrifuge tube, forming a chromogen-developed applicator tip. The color of the chromogen-developed applicator tip is compared to standards on a color-coded chart. The chart is scaled in shades of yellow from LOW (light yellow) corresponding to <0.2 mM $H_2S$ to HIGH (bright yellow) corresponding to >2 mM $H_2S$.

Also by way of example, in an aspect of a method according to the invention, for detecting the presence of VSCs and polyamines in GCF, a GCF sample is obtained by inserting a sterile paper absorbant point into the gingival sulcus and waiting 1 minute for the GCF sample to absorb, thereby forming a GCF-laden paper point. The GCF-laden paper point is then contacted for 5 minutes at room temperature with a volume of 0.1 ml of reagent mixture contained within a sterile, screw-capped 1.5 ml microcentrifuge tube, forming a chromogen-developed paper point. The color of the chromogen-developed paper point is compared to a standard color chart calibrated linearly from 0 (none detectable) to 5 (extreme), corresponding to 2 mM hydrogen sulfide.

Also by way of example, in an aspect of a method according to the invention, VSCs and polyamines are detected and quantified spectrophotometrically through use of the reagent mixture. In a microcentrifuge tube, a GCF-laden paper point is submersed in 450 microliters of 20 mM Tris-HCl, pH 7.75 buffer. When it is desired to perform a spectrophotometric assay according to the invention, a volume of 50 microliters of a 10× concentrated reagent mixture in 50% DMSO, 50 mM imidazole, pH 6.4 buffer containing 1.0 mM $MnCl_2$ is added to and intermixed with the contents of the microcentrifuge tube, and the resultant mixture is incubated at room temperature for 8 minutes. Afterwards, the incubated resultant mixture is transferred to a semi-micro 1.5 ml disposable plastic cuvet, for example by means of a disposable transfer pipette. The concentration of VSC and polyamines is determined by measuring the absorbance of the incubated resultant mixture through use of a spectrophotometer or color/meter and by comparison of the measured absorbance to a reference standard. By measuring the absorbance of a negative control or a blank, background absorbance readings are obtained for use in comparison to the measured absorbance of the incubated resultant mixture.

A method of detection of VSCs and polyamines in GCF according to the invention, such as described in either of the two immediately preceding paragraphs, is observed to possess a lower limit of detection of no more than about 0.02 mM $H_2S$ in a sample, and an upper limit of responsive range near about 2 mM $H_2S$. If the sample contains polyamines but essentially no VSCs, this 0.02 mM lower limit corresponds to a concentration of no more than about 0.02 mM polyamines in the sample. If the sample contains VSCs but essentially no polyamines, this lower limit corresponds to a concentration of no more than about 0.02 mM VSCs in the sample. For detection of polyamines and VSCs according to the invention, a mode of carrying out the invention whereby a composition according to the invention is prepared using, as solvent, reagent grade nanopure water, wherein concentrations of adventitious metals are extremely low, is in general to be preferred.

The invention also provides methods for detection of VSCs and polyamines in saliva and expired breath.

For example, in an aspect of a method according to the invention, for saliva testing, a filter paper disk is impregnated with the reagent mixture by contacting the disk with the reagent mixture, and allowing excess solvent to evaporate, to form an impregnated disk. The impregnated disk is affixed to the bottom interior of a sterile, graduated specimen cup. A volume of saliva is then spit by a subject onto the impregnated disk in the specimen cup. Reaction is allowed to proceed in and on the impregnated disk. After a fixed period of time, the concentration of VSCs and polyamines is determined by comparison of the color developed on the surface of the impregnated disk against a standard such as a scaled color chart.

For example, in an aspect of a method according to the invention, for breath testing, a volume of 0.1 ml of reagent mixture is contacted with a filter paper disk, and excess solvent is allowed to evaporate, to form an impregnated disk. The impregnated disk is then affixed to the distal aperture of a cylindrical tube, said tube having an aperture at each end, the proximal aperture being of such length and width, for example, that a subject might conveniently expire breath through the proximal aperture, and the distal aperture being of such length and width, for example, that the impregnated disk covers the entire distal aperture. A subject then expires breath into the tube through the proximal aperture of the tube and toward the distal aperture of the tube, at least a portion of the expired breath contacting the impregnated disk affixed to the distal aperture of the tube. Reaction is allowed to proceed in and on the impregnated disk. After a fixed period of time, the concentration of VSCs and polyamines is determined by comparison of the color developed on the surface of the impregnated disk against a standard such as a scaled color chart.

While filter paper is an exemplary matrix according to the invention, cotton is also a suitable matrix according to the invention, as is any of a number of other inert matrices, such as those derived from polysaccharides which are low in primary amino groups.

When DTNB and 2-IT are included in a $MnCl_2$-stabilized buffered mixture according to the invention, the levels of two principal classes of anaerobic bacterial waste products are conveniently detected and quantified either visually with a yellow color scale or spectrophotometrically with a calorimeter or spectrophotometer at 412 nm. The simplicity of the use of compositions and methods according to the invention facilitates in-office testing by health care professionals and home testing by patients for halitosis and periodontal disease. Compositions and methods according to the invention thus are useful for the detection of VSCs in samples comprising air, water, oil, or fluids in contact with foodstuffs or foods, and hence are also useful for the detection of products of microbial metabolism, pathogenic microorganisms, halitosis, VSC pollution, or food spoilage or contamination.

The invention provides a diagnostic composition comprising 2-IT, DTNB, a solvent, a buffer, and a metal salt.

The invention provides a neutral diagnostic solution comprising from about 0.1 to about 2.5 millimoles of 2-IT per liter of the solution, from about 0.1 to about 2.5 millimoles of DTNB per liter of the solution, from about 0.02 to about 0.5 millimoles of $MnCl_2$ or $MgCl_2$ or $CoCl_2$ per liter of the solution, and (a) from about 4 to about 100 millimoles of imidazole per liter of the solution or (b) from about 4 to about 100 millimoles of sodium phosphate per liter of the solution.

The invention provides a method of detecting the presence of a VSC or a primary amine in a sample of a physiological fluid, said method comprising the step of contacting the sample with a composition comprising 2-IT, DTNB, a solvent, a buffer, and a metal salt.

The invention provides a method of detecting the presence of a VSC or a primary amine in a sample of a physiological fluid, said method comprising the step of contacting the sample with a neutral diagnostic solution comprising from about 0.1 to about 2.5 millimoles of 2-IT per liter of the solution, from about 0.1 to about 2.5 millimoles of DTNB per liter of the solution, from about 0.02 to about 0.5 millimoles of $MnCl_2$ or $MgCl_2$ or $CoCl_2$ per liter of the solution, and (a) from about 4 to about 100 millimoles of imidazole per liter of the solution or (b) from about 4 to about 100 millimoles of sodium phosphate per liter of the solution.

The invention provides a chromogen, the color of which chromogen develops more rapidly after the chromogen is contacted with a first mixture comprising at least 20 micromolar polyamine or at least 20 micromolar VSC than the color develops in a second mixture identical in composition to the first mixture except that the second mixture comprises no more than 1 micromolar polyamine and no more than 1 micromolar VSC.

The invention provides a chromogen, the color of which chromogen develops more rapidly after the chromogen is contacted with a first mixture comprising at least 20 micromolar polyamine or at least 20 micromolar VSC than the color develops in a second mixture identical in composition to the first mixture except that the second mixture comprises no more than 1 micromolar polyamine and no more than 1 micromolar VSC, wherein a neutral solution of the chromogen has a shelf-life of at least one year.

The invention provides a chromogen, the color of which chromogen develops more rapidly after the chromogen is contacted with a first mixture comprising at least 20 micromolar polyamine or at least 20 micromolar VSC than the color develops in a second mixture identical in composition to the first mixture except that the second mixture comprises no more than 1 micromolar polyamine and no more than 1 micromolar VSC, wherein the color of the developed chromogen is yellow.

The invention provides a chromogen, the color of which chromogen develops more rapidly after the chromogen is contacted with a first mixture comprising at least 20 micromolar polyamine or at least 20 micromolar VSC than the color develops in a second mixture identical in composition to the first mixture except that the second mixture comprises no more than 1 micromolar polyamine and no more than 1 micromolar VSC, wherein the chromogen comprises 2-IT and DTNB.

The invention provides a test kit comprising a chromogen, the color of which chromogen develops more rapidly after the chromogen is contacted with a first mixture comprising at least 20 micromolar polyamine or at least 20 micromolar VSC than the color develops in a second mixture identical in composition to the first mixture except that the second mixture comprises no more than 1 micromolar polyamine and no more than 1 micromolar VSC.

The invention provides a test kit comprising a chromogen, the color of which chromogen develops more rapidly after the chromogen is contacted with a first mixture comprising at least 20 micromolar polyamine or at least 20 micromolar VSC than the color develops in a second mixture identical in composition to the first mixture except that the second mixture comprises no more than 1 micromolar polyamine and no more than 1 micromolar VSC, wherein the test kit has a shelf-life of at least one year.

The invention provides a method of detecting the presence of a microorganism in a sample of a physiological fluid, said method comprising contacting the sample with a chromogen, the color of which chromogen develops more rapidly after the chromogen is contacted with a first mixture comprising at least 20 micromolar polyamine or at least 20 micromolar VSC than the color develops in a second mixture identical in composition to the first mixture except that the second mixture comprises no more than 1 micromolar polyamine and no more than 1 micromolar VSC.

The invention provides a method of detecting the presence of a microorganism in a sample of a physiological fluid, said method comprising contacting the sample with a chromogen, the color of which chromogen develops more rapidly after the chromogen is contacted with a first mixture comprising at least 20 micromolar polyamine or at least 20 micromolar VSC than the color develops in a second mixture identical in composition to the first mixture that the second mixture comprises no more than 1 micromolar polyamine and no more than 1 micromolar VSC, wherein the microorganism is an anaerobe or a facultative aerobe.

The invention provides a method of detecting the presence of a microorganism in a sample of a physiological fluid, said method comprising contacting the sample with a chromogen, the color of which chromogen develops more rapidly after the chromogen is contacted with a first mixture comprising at least 20 micromolar polyamine or at least 20 micromolar VSC than the color develops in a second mixture identical in composition to the first mixture except that the second mixture comprises no more than 1 micromolar polyamine and no more than 1 micromolar VSC, wherein the physiological fluid comprises GCF, saliva, tongue scrapings, or expired breath.

It will therefore be readily understood by those persons skilled in the art that the invention is susceptible of a broad utility and application. Many embodiments and adaptations of the invention other than those herein described, as well as many variations, modifications and equivalent arrangements, will be apparent from or reasonably suggested by the present invention and the foregoing description thereof, without departing from the substance or scope of the present invention. Accordingly, while the invention has been described herein in detail in relation to its preferred embodiment, it is to be understood that this disclosure is only illustrative and exemplary of the invention and is made merely for purposes of providing a full and enabling disclosure of the invention. The foregoing disclosure is not intended or to be construed to limit the invention or otherwise to exclude any such other embodiments, adaptations, variations, modifications or equivalent arrangements, the invention being limited only by the claims appended hereto and the equivalents thereof.

The invention claimed is:

1. A matrix impregnated with a chromogenic composition useful for the detection of volatile sulfur compounds (VSCs), comprising DTNB, a buffer, and highly purified water as solvent, wherein the matrix is selected from matrices that are inert and low in primary amino groups.

2. A matrix of claim 1, wherein the matrix is a filter paper disk.

3. A matrix of claim 1, wherein the matrix is cotton.

4. A matrix of claim 1, wherein the matrix is a polysaccharide.

5. The matrix of claim 1, wherein the composition is stable for 12 months at room temperature.

* * * * *